(12) United States Patent
Breton et al.

(10) Patent No.: US 6,962,712 B2
(45) Date of Patent: Nov. 8, 2005

(54) COSMETIC OR DERMATOLOGICAL COMPOSITION COMPRISING OF A COMBINATION OF AN ELASTASE INHIBITOR OF THE N-ACYLAMINOAMIDE FAMILY AND AT LEAST ONE ANTIFUNGAL AGENT OR AT LEAST ONE ANTIBACTERIAL AGENT

(75) Inventors: Lionel Breton, Versailles (FR); Yann Mahe, Morsang sur Orge (FR)

(73) Assignee: L'Oreal, Paris (FR)

( * ) Notice: Subject to any disclaimer, the term of this patent is extended or adjusted under 35 U.S.C. 154(b) by 98 days.

(21) Appl. No.: 10/179,983

(22) Filed: Jun. 26, 2002

(65) Prior Publication Data

US 2003/0152596 A1 Aug. 14, 2003

(30) Foreign Application Priority Data

Jun. 26, 2001 (FR) ............................................ 01 08432

(51) Int. Cl.$^7$ ............................ A61K 9/00; A61K 7/42; A61K 7/06; A61K 31/74; A01N 37/18
(52) U.S. Cl. ........................ 424/401; 424/59; 424/70.1; 424/78.02; 424/78.07; 514/2; 514/119; 514/568
(58) Field of Search ................................ 424/400, 401, 424/59, 70.1, 78.02, 78.07, 600, 641, 642, 702; 514/2, 844

(56) References Cited

U.S. PATENT DOCUMENTS

| 5,234,909 | A | | 8/1993 | Philippe | |
|---|---|---|---|---|---|
| 5,965,145 | A | * | 10/1999 | Marion et al. | 424/401 |
| 6,071,543 | A | * | 6/2000 | Thornfeldt | 424/642 |
| 2003/0152600 | A1 | * | 8/2003 | Dalko et al. | 424/401 |

FOREIGN PATENT DOCUMENTS

| JP | 2000-178163 | * | 6/2000 |
|---|---|---|---|
| WO | WO 00/12467 | | 3/2000 |

OTHER PUBLICATIONS

Patent Abstracts of Japan; vol. 15, No. 001; Jan. 7, 1991; & JP 02 256609; Oct. 17, 1990.

M. Nakamura et al; "A Two–Step, One–Pot Synthesis of Diverse N–Pyruvoyl Amino Acid Derivatives Using the Ugl Reaction"; Bioorganic & Medicinal Chemistry Letters 10 (2000) 2807–2810.

* cited by examiner

*Primary Examiner*—Gary Kunz
*Assistant Examiner*—Sharmila S. Gollamudi
(74) *Attorney, Agent, or Firm*—Oblon, Spivak, McClelland, Maier & Neustadt, P.C.

(57) ABSTRACT

Cosmetic or dermatological composition characterized in that it comprises a combination of an elastase inhibitor of the N-acylaminoamide family and at least one antifungal agent or at least one antibacterial agent.

19 Claims, No Drawings

COSMETIC OR DERMATOLOGICAL COMPOSITION COMPRISING OF A COMBINATION OF AN ELASTASE INHIBITOR OF THE N-ACYLAMINOAMIDE FAMILY AND AT LEAST ONE ANTIFUNGAL AGENT OR AT LEAST ONE ANTIBACTERIAL AGENT

The present invention relates to the field of cosmetic or dermatological compositions. It relates to novel cosmetic or dermatological compositions comprising a combination of an inhibitor of elastase of the N-acylaminoamide family and at least one antifungal agent or at least one antibacterial agent. This composition is preferably designed to improve the cutaneous signs of ageing and/or photo-ageing, and in particular wrinkles, by retarding the adverse changes of the conjunctive tissue and by improving the functional state of the skin while controlling the excess of resident bacteria and/or yeasts and/or pathogens.

The human skin is constituted of two compartments, namely a superficial compartment, the epidermis, and a deep compartment, the dermis. The natural human epidermis is composed principally of three types of cells which are the keratinocytes, very largely predominant, the melanocytes and the cells of Langerhans. Each of these cell types contributes as a result of its intrinsic functions to the essential role played in the organism by the skin.

The dermis provides the epidermis with a solid support. It is also its nutritive element. It is constituted mainly of fibroblasts and of an extracellular matrix itself composed principally of collagen, elastin and a substance called ground substance, compounds synthesized by the fibroblasts. Leukocytes, mastocytes or also tissue macrophages are also found there. Blood vessels and nerve fibres also pass through it.

It is known that when subject to a superficial cutaneous stress, which can in particular be of chemical, physical or bacterial origin, the keratinocytes of the superficial layers of the epidermis release biological mediators which possess the capacity to attract certain infiltrating cells of the skin, themselves responsible for the maintenance of a transient local irritation.

Of the biological mediators capable of being produced by the thus stressed keratinocytes, mention should be made of the chemokines which are chemoattractive cytokines responsible for the recruitment of leukocytes at the sites of inflammation, including interleukin 8 (IL-8) which is more particularly responsible for the recruitment of neutrophils.

These cells infiltrating the irritated or aggressed areas then release enzymes among which mention may be made of leukocyte elastase. As a result of the action of this enzyme in particular the elastin fibres of extracellular support of the conjunctive tissue can be degraded and thus lead to a diminution of the elasticity of the skin.

Moreover it is even known that in synergy with cathepsin G, the leukocyte elastase can dissociate the integrity of the epidermis by enlarging the interkeratinocytic intercellular spaces.

Thus, in the long-term, the sum of the cutaneous micro-stresses, generated for example by ageing or by prolonged exposure to the UV (in this case, it is called photo-ageing) can lead to a more or less accelerated loss of the natural elasticity of the skin. The network formed by the elastic fibres of the underlying conjunctive tissue and the extracellular spaces can then be progressively disrupted. This is followed by accelerated ageing of the skin (wrinkled and/or less supple skin) via the impairment of the dermal elastic network as well as an accentuation of the wrinkles (deeper wrinkles).

As a result of the action of elastase, the elastin fibres of extracellular support of the conjunctive tissue are degraded. In synergy with cathepsin G, the leukocyte elastase can even dissociate the integrity of the epidermis by enlarging the interkeratinocyte intercellular spaces (Ludolph-Hauser et al. Exp. Dermatol, 1999 8 (1) 46–52). The leukocyte elastase has recently been held responsible for the maintenance of scabs and the occurrence of venous ulcers of the legs owing to its ability to degrade fibronectin (Herrick S et al. Lab. Invest. 1997 (3) 281–288). The sum of the localised degradative micro-stresses (subsequent for example to prolonged exposure to the sun) can result in the long term in an accelerated loss of the natural elasticity of the skin. The network of elastic fibres of the underlying conjunctive tissue and the extracellular spaces is then progressively disrupted. This accelerated degradation can proceed together with the process of normal ageing of the skin which is characterized by a greater sensitivity of the elastin fibres to the action of elastase (Stadler R & Orfanos C E Arch. Dermatol. Res. 1978 262 (1) 97–111.

It is known in the state of the art that molecules capable of retarding the degradative activity of the elastic fibres of the intercellular spaces can be introduced into the cutaneous tissue.

The object of the present invention is to suggest a solution for these different problems, and in particular to suggest novel compounds capable of being used as cosmetics or pharmaceutical agents for limiting the ageing of the skin, whether chronobiological or photo-induced, and in particular ageing generated by a diminution of the elasticity of the skin and/or by degradation of the collagen in the structure of the tissues.

It has been shown according to the invention that the problems related to the cutaneous signs of ageing and/or photo-ageing associated with the absence of control of the excess of resident and/or pathogenic bacteria and/or yeasts can be resolved, or at the very least significantly improved, by the combination of an elastase inhibitor of the N-acylaminoamide family and at least one antifungal agent or at least one antibacterial agent.

Consequently, the object of the invention is a cosmetic or dermatological composition characterized in that it comprises a combination between an inhibitor of elastase of the N-acylaminoamide family and at least one antifungal agent or at least one antibacterial agent.

Another object of the invention consists in a cosmetic treatment method for the skin of the body or face, including the scalp, in which a cosmetic composition such as defined above is applied to the skin.

It has in fact been observed that the compounds of formula (I) possess an inhibitory activity of the activity of the elastases and that they can hence be used to limit and/or control the degradation of the elastin fibres.

It follows from that that they can be used in or for the preparation of a composition, the compounds or the composition being designed to treat the cutaneous signs of ageing preventively and/or curatively.

The novel combination of the N-acylaminoamide compounds with at least one antimicrobial agent or at least one antifungal agent makes it possible to significantly reinforce the anti-ageing effect of the matrix tissue by the application of an antimicrobial and antifungal effect. Thus, as a result of a specific action on the excess of cutaneous microflora, the compositions according to the invention diminish appreciably the micro-inflammatory processes associated with this adverse change in the microflora which can contribute in particular to premature ageing of the epidermal function.

According to the invention, the regulatory element of elastase activity (i.e. the N-acylaminoamide derivative inhibitor of the enzymatic activity of leukocyte elastase {2-[acetyl-(3-trifluoromethyl-phenyl)-amino]-3-methyl-butyrylamino}acetic acid) is combined with one or more active agents capable of regulating the proliferation of the cutaneous micro-organisms.

The composition obtained is intended for the treatment of ageing disorders and/or to be more specifically designed to treat all of the skin disorders associated with too great a proliferation of cutaneous bacteria and/or yeasts (P. Ovale, P. Acnes, A. Aureus).

Preferably, this novel combination is used in care and/or hygiene cosmetic preparations for the areas exposed to the sun (scalp, body, face, lips), in care and/or hygiene cosmetic preparations of ulcerated areas, in toothpastes or mouth washes and, generally, in all of the so-called "anti-skin ageing" cosmetic preparations which have as objective the retardation of the chronobiological disruption of the supporting tissue and of the architecture of the cutaneous matrix elements. More particularly, this combination should be reserved for comedone- and acne-infected skins.

Without wanting to be bound by any theory, the applicant considers that the fact to supply at the level of the keratinocytes of the superficial layers of the skin compounds capable of retarding the degradative activity of the elastic fibres of the intercellular spaces may make it possible to diminish this phenomenon of accelerated skin ageing, due to superficial cutaneous stresses and that the combination of these compounds with an antimicrobial agent or an antifungal agent considerably reinforces their effects.

Preferred N-acylamino-amide Compounds

The compounds susceptible to being used in the present invention thus conform to the following formula (I):

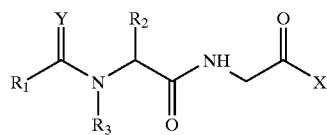

(I)

in which:
the radical Y represents O or S,
the radical R1 represents:
  (i) a hydrogen atom
  (ii) a hydrocarbon radical, linear, branched or cyclic, saturated or unsaturated, containing 1 to 18 carbon atoms,
optionally substituted by 1 to 5 groups, identical or different, selected from
—OH; —OR; —O—COR; —SH; —SR; —S—COR; —NH$_2$; —NHR; —NRR'; —NH—COR; -Hal (halogen); —CN; —COOR; —COR; —P(O)—(OR)$_2$; —SO$_2$—OR;
with R and R' representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing independently a hydrocarbon radical, linear, branched or cyclic, saturated or unsaturated, containing 1 to 6 carbon atoms, optionally halogenated, even perhalogenated;
  (iii) a radical selected from the radicals —OR; —NH$_2$; —NHR; —NRR'; —NH—COR; —COOR; —COR;
with R and R' representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;
the radical R2 represents a hydrocarbon radical, linear, branched or cyclic saturated or unsaturated, containing 1 to 18 carbon atoms,
optionally substituted by 1 to 5 groups, identical or different, selected from
—OH; —OR; —O—COR; —SH; —SR; —S—COR; —NH$_2$; —NHR; —NRR'; —NH—COR; -Hal (halogen); —CN; —COOR; —COR;
with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;
the radical R3 represents a radical selected from those of formula (II) or (III)

  (II)

  (III)

in which:
  y is an integer included between 0 and 5, and y' is an integer included between 1 and 5;
  A is a divalent hydrocarbon radical, linear, branched or cyclic, saturated or unsaturated, containing 1 to 18 carbon atoms,
optionally substituted by 1 to 5 groups, identical or different, selected from
—OH; —OR; —O—COR; —SH; —SR; —S—COR; —NH$_2$; —NHR; —NRR'; —NH—COR; -Hal (halogen, even perhalogen); —CN; —COOR; —COR; —NO$_2$; —SO$_2$—OR;
with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5 or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

B is a hydrocarbon radical, linear, branched or cyclic, saturated or unsaturated, containing 1 to 18 carbon atoms, optionally substituted by 1 to 5 groups, identical or different, selected from
—OH; —OR; —O—COR; —SH; —SR; —S—COR; —NH$_2$; —NHR; —NRR'; —NH—COR; -Hal (halogen, even perhalogen); —CN; —COOR; —COR; —NO$_2$; —SO$_2$—OR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

the radical X represents a radical selected from —OH; —OR$_4$, —NH$_2$, —NHR$_4$, NR$_4$R$_5$, —SR$_4$, —COOR$_4$; —COR$_4$;

With R$_4$ and R$_5$ each representing independently a hydrocarbon radical, linear, branched or cyclic, saturated or unsaturated, containing 1 to 6 carbon atoms, optionally substituted by 1 to 5 groups, identical or different, selected from
—OH; —OR; —O—COR; —SH; —SR; —S—COR; —NH$_2$; —NHR; —NRR'; —NH—COR; -Hal (halogen, even perhalogen); —CN; —COOR; —COR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5 or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

the said R$_4$ and R$_5$ radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

Also included in this definition are the mineral or organic acid salts of said compounds as well as their optical isomers, in isolated form or as a racemic mixture.

By hydrocarbon radical, linear, cyclic or branched, is meant in particular the radicals of the alkyl, aryl, aralkyl, alkylaryl, alkenyl and alkynyl type.

The group $C_6H_5$ present in the radical R3 must be understood as a cyclic aromatic group.

Preferably, the radical Y represents oxygen.

Preferably, the radical R1 represents hydrogen or a hydrocarbon radical, linear or branched, saturated or unsaturated, containing 1 to 12, and in particular 1, 2, 3, 4, 5 or 6 carbon atoms, optionally substituted.

In particular, the substituents may be selected from —OH, —OR and/or —P(O)—(OR)$_2$ with R representing a hydrocarbon radical, linear, branched or cyclic, saturated or unsaturated, containing 1 to 6 carbon atoms, optionally halogenated, even perhalogenated.

Preferably, the radical R1 represents a methyl, ethyl, propyl or isopropyl radical, optionally substituted by a —OH or —P(O)—(OR)$_2$ group with R representing methyl, ethyl, propyl or isopropyl.

Preferably, the radical R2 represents a hydrocarbon radical, linear or branched, saturated or unsaturated, containing 1 to 12, and in particular 1, 2, 3, 4, 5 or 6 carbon atoms, optionally substituted.

In particular, the substituents may be selected from —OH and —OR with R representing a hydrocarbon radical, linear, branched or cyclic, saturated or unsaturated, containing 1 to 6 carbon atoms, optionally halogenated, even perhalogenated.

Preferably, the radical R2 represents a methyl, ethyl, propyl, isopropyl, n-butyl, tert.butyl or isobutyl radical.

Preferably, the radical R3 represents a radical of formula —$C_6H_{(5-y')}$—B$_{y'}$ for which y'=1, 2 or 3; or a radical of formula -A-$C_6H_{(5-y)}$—B$_y$ for which y=0, 1 or 2.

Preferably, A is a divalent hydrocarbon radical, linear or branched, saturated or unsaturated, containing 1 to 12 carbon atoms, optionally substituted.

The substituents of A are preferably selected from -Hal (halogen, even perhalogen); —CN; —COOR; —NO$_2$; —SO$_2$—OR; with R representing a hydrocarbon radical, linear, branched or cyclic, saturated or unsaturated, containing 1 to 6 carbon atoms, optionally halogenated, even perhalogenated.

Preferably, B is a hydrocarbon radical, linear or branched, saturated or unsaturated, containing 1 to 12 carbon atoms, optionally substituted.

The substituents of B are preferably selected from -Hal (halogen, even perhalogen); —CN; —COOR; —NO$_2$; —SO$_2$—OR; with R representing a hydrocarbon radical, linear, branched or cyclic, saturated or unsaturated, containing 1 to 6 carbon atoms, optionally halogenated, even perhalogenated.

Preferably, the radical R3 represents a group selected from one of the following formulae:

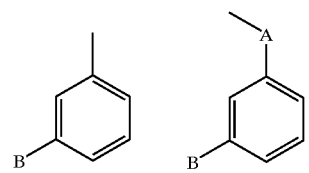

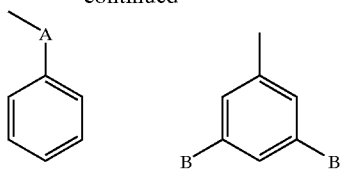

In which A and B have the above meanings.

In particular, the divalent radical A may be methylene, ethylene, propylene.

The radical B is preferably a methyl, ethyl, propyl or isopropyl radical, substituted by one or more halogens, in particular chlorine, bromine, iodine or fluorine, and preferably completely halogenated (perhalogenated), such as perfluorinated. Particular mention may be made of the perfluoromethyl radical (—CF3) as very particularly preferred.

Preferably, the radical X represents a radical selected from —OH or —OR$_4$ with R$_4$ representing a hydrocarbon radical, linear, cyclic or branched, saturated or unsaturated, containing 1 to 6 carbon atoms, optionally substituted.

The substituents may be selected from —OH and —OR with R representing a hydrocarbon radical, linear, branched or cyclic, saturated or unsaturated, containing 1 to 6 carbon atoms, optionally halogenated, even perhalogenated.

Preferably, the radical X represents a radical selected from —OH, —OCH$_3$, —OC$_2$H$_5$, —O—C$_3$H$_7$ or —OC$_4$H$_9$.

Of the particularly preferred compounds mention may be made of:

{2-[acetyl-(3-trifluoromethyl-phenyl)-amino]-3-methyl-butyrylamino}acetic acid

{2-[acetyl-(3-trifluoromethyl-phenyl)-amino]-3-methyl-butyrylamino}ethyl acetate

[2-(acetyl-benzyl-amino)-3-methyl-butyrylamino]acetic acid

[2-(acetyl-benzyl-amino)-3-methyl-butyrylamino]ethyl acetate (2-{benzyl-[(diethoxy-phosphoryl)-acetyl]-amino}-3-methyl-butyrylamino)ethyl acetate.

The compounds according to the invention can be easily prepared by the specialist skilled in the art on the basis of his general knowledge. In particular, it is possible to react a carboxylic acid, an aldehyde, an amino compound and an isonitrile according to the Ugi reaction.

It is dearly understood that during the synthesis of the compounds according to the invention and as a function of the nature of the different radicals present in the starting compounds, the specialist will take care to protect certain substituents in order that they do not reaction in the course of the reactions.

The quantity of compound to be used in the compositions according to the invention can easily be determined by the specialist skilled in the art as a function of the nature of the compound used, the person to be treated and/or the effect desired. Generally, this quantity may be comprised between 0.00001 and 20% by weight of the total weight of the composition, and preferably between 0.001 and 10% by weight.

The compounds of formula (I) may in particular be used, alone or as a mixture, in a composition which comprises a physiologically acceptable medium, in particular in a cosmetic or pharmaceutical composition which hence comprises moreover a cosmetically or pharmaceutically acceptable medium.

The physiologically acceptable medium in which the compounds according to the invention may be used as well as its constituents, their quantity, the formulation of the composition and its method of preparation can be chosen by the specialist skilled in the art on the basis of his general knowledge as a function of the type of composition desired.

Generally speaking, this medium can be anhydrous or aqueous. Thus it may comprise an aqueous phase and/or a fatty phase.

Preferred Antifungal Agents

According to the invention, by antifungal agent is meant any substance capable of inhibiting or preventing the growth of yeasts, in particular those that are found at the surface of the epidermis rich in sebaceous glands and particularly at the surface of the scalp like for example Pityrosporum ovale and its varieties (Pityrosporum orbiculare and Malassezia furfur).

Of the antifungal agents used according to the invention more particular mention may be made of terbinafine, zinc pirythione, selenium sulfide, the tars and their derivatives, undecylenic acid and its salts, hydroxypyridone derivatives such as CICLOPIROX: 6-cyclohexyl 1-hydroxy 4-methyl 2-(1H)-pyridone or OCTOPIROX: 1-hydroxy 4-methyl 6-(2,4,4-trimethylpentyl)-2-(1H)-pyridone, imidazole agents such as ketoconazole, flutrinazole, neticonazole, setaconazole nitrate, omoconazole nitrate, fenticonazole nitrate, omoconazole, butoconazole nitrate, sulconazole nitrate, bifonazole, oxiconazole nitrate, troconazole, triazole derivatives such as terconazole, fluconazole and itraconazole, terbinafine, butenafine.

These antifungal agents are preferably present in the compositions conforming to the invention at a concentration which may vary from about 0.0001 to 10% by weight of the total weight of the composition. Even more preferably the concentration of antifungal agents may vary from 0.01 to 2% by weight of the total weight of the composition.

Preferred Antibacterial Agents

A first family of antibacterial compounds is constituted of honey and its derivatives, which have been shown to modify the attachment of the micro-organisms to the cells, in particular to the cells of the skin and/or the mucous membranes.

By honey is meant the transformation product created by bees from the nectar and/or honeydew of flowers.

Although the content of the various constituents may vary according to its source, the honey is usually at least a mixture of glucose, levulose, maltose, sucrose as well as other constituents like proteins, organic acids, lactoses, mineral substances, trace elements, vitamins, many enzymes, aromatic substances and, of course, water.

The honey may be an unfermented honey not containing hydroxyacids or a fermented honey containing hydroxyacids.

The honey can be of any source. In particular, it may be honey derived from the flowers of acacia, lime, lavender, chestnut, conifers, orange trees, all types of mountain flowers, flowers from the "Gatinais".

Preferably, honey of acacia flowers is used according to the invention.

By honey of acacia flowers is meant any honey obtained from the nectar and/or honeydew of Robinier (*Robinia pseudacacia* L.) flowers.

The quantity of honey usable according to the invention obviously depends on the effect desired and must be in an efficacious quantity to prevent partially, even totally, the adhesion of the micro-organisms or to facilitate the detachment of micro-organisms.

A second family of preferred antibacterial compounds according to the invention consists of compounds of the hydroxystilbene family.

Hydroxystilbenes should preferably be used which comply with the general formula below (IV):

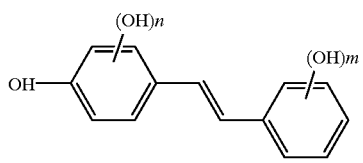

In which n is an integer included between 1 and 4 inclusively and m is an integer comprised between 1 and 5 inclusively. These compounds may be in the cis or trans form.

According to the invention the term hydroxystilbene covers both the compounds of formula I and their hydroxyalkylated derivatives.

The hydroxystilbenes are compounds that are found in the natural state in the plants of the class of the spermatophytes and in particular the vine. Compounds like for example the resveratrol are found in the grape and in wine.

According to the invention the hydroxystilbenes can be used alone or in mixtures of any kind and may be of natural or synthetic origin.

The hydroxystilbenes usable according to the invention are preferably selected from:
4'-hydroxystilbene,
2',4'-dihydroxystilbene,
3',4'-dihydroxystilbene,
4',4'-dihydroxystilbene,
2',4',4'-trihydroxystilbene,
3',4',4'-trihydroxystilbene,
2,4,4'-trihydroxystilbene,
3,4,4'-trihydroxystilbene,
3,4',5trihydroxystilbene, (or resveratrol)
2',3,4-trihydroxystilbene,
2,3',4-trihydroxystilbene,
2',2,4'-trihydroxystilbene,
2,4,4',5-tetrahydroxystilbene
2',3,4',5-tetrahydroxystilbene,
2,2',4,4'-tetrahydroxystilbene,
3,3',4',5-tetrahydroxystilbene
2,3',4,4'-tetrahydroxystilbene,
3,3',4,4'-tetrahydroxystilbene,
3,3',4',5,5'-pentahydroxystilbene,
2,2',4,4',6-pentahydroxystilbene
2,3',4,4',6-pentahydroxystilbene,
2,2',4,4',6,6'-hexahydroxystilbene In a very preferred manner, 3,4',5-trihydroxystilbene (or resveratrol) is used according to the invention.

A third family of antibacterial compounds usable according to the invention are halogenated antibacterial compounds.

According to the invention, by halogenated antibacterial agent is meant any substance bearing at least one halogen atom and one capable of inhibiting or preventing the growth of the bacterial flora present at the surface of the epidermis rich in sebaceous glands.

Of the halogenated antibacterial agents used according to the invention, more particular mention may be made of the chlorinated antibacterial agents such as Triclosan which is 5-chloro-2-(2,4-dichlorophenoxy)phenol, sold under the trade name IRGASAN by the CIBA-GEIGY company, chlorhexidine and its derivatives and chloramphenicol.

Of the other anti-bacterial agents preferably used according to the invention, mention may be made of complexes sugars and in particular syallyllactose capable of limiting in particular the multiplication of *Helicobacter pylori*. By analogy, combinations of antibiotics which have demonstrated more particularly very good efficacity in inhibiting *H. pylori* in other pathologies. Like the pharmaceutical combinations (omeprazole/amoxicillin) or pharmaceutical agents like metrodinazole, clarithromycin are described by Miehjike et al. In Digestion (1988) 59 (6): 646–50.

The antibacterial agents are preferably present at a concentration included between 0.001% and 10% of the total weight of the composition, and preferably between 0.01% and 2%.

The preferably the weight ratio of the antifungal agent to the antibacterial agent varies from 0.2 to 10.

The combination of at least one N-acylamino-amide compound and at least one antibacterial agent and/or at least one antifungal agent can in particular be used, alone or in a mixture, in a composition which comprises a physiologically acceptable medium, in particular in a cosmetic or pharmaceutical composition which thus in addition comprises a cosmetically or pharmaceutically acceptable medium.

The physiologically acceptable medium in which the compounds according to the invention can be used as well as its constituents, their quantity, the formulation of the composition and its method of preparation can be chosen by the specialist skilled in the art on the basis of his general knowledge as a function of the type of composition desired.

Generally speaking, this medium can be anhydrous or aqueous. Thus it may comprise an aqueous phase and/or a fatty phase.

For an application to the skin, the composition may have the form in particular of an aqueous or oily solution; of a dispersion of the lotion or serum type; of emulsions of liquid or semi-liquid consistency of the milk type obtained by dispersion of a fatty phase in an aqueous phase (O/W) or the reverse (W/O); of suspensions or emulsions of soft consistency of the cream type or aqueous or anhydrous gels; of microcapsules or microparticles; vesicular dispersions of the ionic and/or non-ionic type.

For an application to the hair the composition may be in the form of aqueous, alcoholic or aqueous-alcoholic solutions; in the form of creams, gels, emulsions, foams; in the form of compositions for aerosol also comprising a propellant under pressure.

When the composition is available in aqueous form, in particular in the form of a dispersion, emulsion or aqueous solution, it can comprise an aqueous phase which may contain water, floral water and/or mineral water.

Said aqueous phase may comprise in addition alcohols such as $C_1$–$C_5$ monoalcohols and/or polyols such as glycerol, butyleneglycol, isoprene glycol, propylene glycol, polyethyleneglycol.

When the composition according to the invention is available in the form of an emulsion, it may optionally comprise in addition a surfactant, preferably in a quantity of 0.01 to 30% by weight compared with the total weight of the composition. The composition according to the invention may also comprise at least one coemulsifier which may be selected from oxyethylenated sorbitan monostearate, fatty alcohols such as stearyl alcohol or cetyl alcohol, or esters of fatty acids and polyols such as glyceryl stearate.

The composition according to the invention may also comprise a fatty phase, in particular constituted of fatty bodies liquid at 25° C., such as animal, vegetable, mineral or synthetic oils, volatile or not; fatty bodies solid at 25° C. such as waxes of animal, vegetable, mineral or synthetic origin; pasty fatty bodies; gums; their mixtures.

The volatile oils are usually oils with a saturating vapour pressure at least equal to 0.5 millibar (i.e. 50 Pa).

Of the constituents of the fatty phase mention may be made of:

- the cyclic volatile silicones with 3 to 8, and preferably 4 to 6, silicon atoms,
- the cyclocopolymers of the dimethylsiloxane/methylalkylsiloxane type,
- the linear volatile silicones with from 2 to 9 silicon atoms
- the hydrocarbon volatile oils, such as the isoparaffins and in particular isododecane and fluorinated oils.
- the polyalkyl (C1–C20) siloxanes and in particular those with terminal trimethylsilyl groups, among which may be mentioned the linear polydimethylsiloxanes and the alkylmethylpolysiloxanes such as cetyldimethicone (designation CTFA),
- the silicones modified by aliphatic and/or aromatic groups, optionally fluorinated, or by functional groups such as hydroxyl, thiol and/or amine groups.
- the phenylated silicone oils,
- the oils of animal, vegetable or mineral origin, and in particular the animal or vegetable oils formed by fatty acid esters and polyols, in particular the liquid triglycerides, for example, the oils of sunflower, maize, soya, squash, grapeseed, sesame, hazelnut, apricot, almond or avocado; the fish oils, glycerol tricaprocaprylate, or the vegetable or animal oils of formula. R1COOR$_2$ in which R1 represents a higher fatty acid residue containing from 7 to 19 carbon atoms and R$_2$ represents a branched hydrocarbon chain containing from 3 to 20 carbon atoms, for example Purcellin oil, paraffin oil, vaseline oil, perhydrosqualene, the oils of wheat germ, calophylium, sesame, macadamia, grapeseed, colza, coconut, peanut, palm, castor oil, jojoba oil, olive oil or cereal germ oil; fatty acid esters; alcohols; acetylglycerides; octanoates, decanoates or ricinoleates of alcohols or polyalcohols; triglycerides of fatty acids; glycerides;
- the fluorinated and perfluorinated oils
- the silicone gums;
- the waxes of animal, vegetable, mineral or synthetic origin such as the microcrystalline waxes, paraffin, petrolatum, vaseline, ozokerite, montan wax; beeswax, lanolin and its derivatives; candellila wax, ouricury wax, carnauba wax, Japan wax, cocoa butter, the waxes of cork fibres or sugar cane; the hydrogenated oils solid at 25° C., the ozokerites, the fatty esters and glycerides solid at 25° C.; the polyethylene waxes and the waxes obtained by Fischer-Tropsch synthesis; hydrogenated oils solid at 25° C.; lanolins; fatty esters solid at 25° C.; the silicone waxes; the fluorinated waxes. In a known manner, the composition according to the invention may comprise the usual adjuvants in the field under consideration such as the hydrophilic or lipophilic gelling agents, hydrophilic or lipophilic additives, active compounds in particular cosmetic or pharmaceutical hydrophilic or lipophilic active agents, the preservatives, the antioxidants, the solvents, the perfumes, the fillers, the pigments, the pearlescent agents, the UV filters, the odour absorbers and the colouring matters. These adjuvants according to their nature may be introduced into the fatty phase, in the aqueous phase and/or in lipid microspheres.

The nature and the quantity of these adjuvants may be selected by the specialist skilled in the art on the basis of his general knowledge so as to obtain the desired form of presentation for the composition. In any case the specialist skilled in the art will take care to choose all of optional additional compounds and/or their quantity such that the advantageous properties of the composition according to the invention are not, or not substantially, impaired by the addition considered.

The cosmetic or pharmaceutical compositions according to the invention may be presented in particular in the form of a composition designed for the care and/or treatment of ulcerated areas or areas subjected to a cutaneous stress or microstress, in particular generated by exposure to UV and/or by being placed in contact with a irritant product.

Thus, the compositions according to the invention may be presented in particular in the form of:

- a product for the care, treatment, cleansing or protection of the skin of the face or body including the scalp, such as a care composition (daytime, nighttime, hydrating) for the face or body; an anti-wrinkle or anti-age composition for the face; a composition rendering the face mat; a composition for irritated skin; a composition for the removal of make-up; a milk for the body, in particular a hydrating milk, optionally after exposure to the sun;
- a sun protection composition, an artificial tanning composition (self-tanning) or care composition after exposure to the sun;
- a composition for the hair, and in particular a sun protection cream or gel; a care composition for the scalp, in particular against hair loss or stimulating hair growth; antiparasitic shampooing;
- a product for the make-up of the skin or the face, body or lips, such as foundation make-up, complexion cream, rouge or eyelid make-up, a free or compact powder, anti-shadow stick, a camouflaging stick, a lipstick, a lip care composition;
- a product for buccal hygiene such as toothpaste or a mouthwash.

The compositions according to the invention find a preferred application as care composition of the facial skin, of the anti-wrinkle or anti-age type, and as composition for sun protection or après soleil.

The object of the present invention is also a cosmetic treatment method for the skin of the body or face, including the scalp, in which a cosmetic composition containing a combination of a compound of the N-acylamino-amide family and at least one antibacterial agent or at least one antifungal agent, left in contact then optionally rinsed.

The cosmetic treatment method of the invention may be used in particular by applying the cosmetic compositions such as defined above according to the usual procedure for the use of these compositions. For example: application of creams, gals, serums, lotions, make-up removal milks or anti-sun compositions to the skin or the dry hair; application of a lotion for the scalp to wet hair; application of toothpaste to the gums.

The invention is illustrated in more detail in the following examples.

EXAMPLE 1

Preparation of {2-[acetyl-(3-trifluoromethyl-phenyl)-amino]-3-methyl-butyrylamino}ethyl acetate of the formula

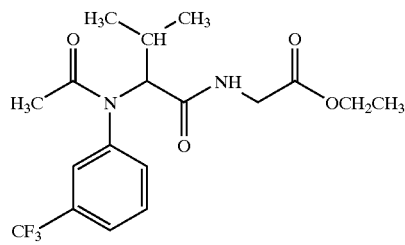

0.63 ml of isobutyraldehyde and 1 ml of trifluoromethylamine (1.15 eq) are mixed in 15 ml of methanol with stirring. The mixture is left to react for 15 minutes at 20° C., then 0.46 ml of acetic acid (1.15 eq) is added and the mixture is allowed to react for 10 minutes at 20° C. Then 0.8 ml of 95% ethyl isocyanoacetate (1 eq) is added and reaction is allowed to proceed for 48 hours at 20° C.

The reaction mixture is concentrated at the rotovapor and the residue is purified on a column of silica (eluant: heptane: 3/ethyl acetate: 7; Rf=0.5). 2.45 g of compound are obtained in the form of a waxy solid, hence in a yield of 91%.

$^1$H NMR (200 MHz; CDCl3) δ ppm: 0.9 (6H; q), 1.3 (3H; t), 1.8 (3H; s), 2.3 (1H; m), 4.0 (2H; q), 4.2 (2H; q), 4.4 (2H; d), 7.3 (1H; t), 7.5 (4H; m)

EXAMPLE 2

Preparation of {2-[acetyl-(3-trifluoromethyl-phenyl)-amino]-3-methyl-butyrylamino}acetic acid of the formula

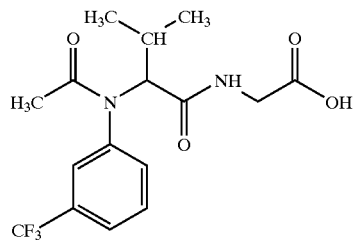

2 g of the compound prepared in Example 1 are dissolved in 30 ml of acetone.

30 ml of 2N sodium hydroxide are added and reaction is allowed to proceed for 6 hours at 20° C. The reaction mixture is concentrated at the rotovapor. The residual aqueous phase is acidified to pH 2 by the addition of concentrated HCl and extracted with CH2Cl2.

The organic phase is concentrated to dryness after being dried over sodium sulfate.

A residue is obtained which is dissolved in a mixture of basic water containing 10% ethanol, then acidified again to pH2 with concentrated HCl. The solution is extracted again with CH2Cl2 and the organic phase is dried over sodium sulfate. It is filtered and concentrated to dryness under vacuum in a rotovapor.

1.3 g of compound are obtained in the form of a slightly light brown solid in a yield of 70%.

$^1$H NMR (200 MHz; DMSO) δ ppm: 0.9 (6H; q), 3.7 (2H; m), 1.8 (4H; m), 4.8 (2H; d), 7.6 (4H; m), 8.4 (1H; t), 12.5 (1H; s)

EXAMPLE 3

The anti-elastase activity of compounds according to the invention was determined in vitro against human leukocyte elastase (HLE)

The test was performed in the following manner:

A substrate Me-OSAAPV-p-NA (methyl-O-succinate alanine alanine proline valine-p-nitroanilide) to which is added the HLE (40 milliunits per ml) and 0.1% of the test compound is incubated at 37° C. for 60 minutes.

The % of inhibition of the elastase activity tested is then determined by spectrophotometry.

The following compounds were tested:
Compound A: {2-[acetyl-(3-trifluoromethyl-phenyl)-amino]-3-methyl-butyrylamino}acetic acid
Compound B: (2-{benzyl-[(diethoxy-phosphoryl)-acetyl]-amino}-3-methyl-butyryl-amino)ethyl acetate
Compound C: [2-(acetyl-benzyl-amino)-3-methyl-butyrylamino]acetic acid
Compound D: [2-(acetyl-benzyl-amino)-3-methyl-butyrylamino]ethyl acetate
The following results were obtained:

| Compound (concentration: 0.1%) | % inhibition of elastase activity tested |
|---|---|
| Compound A | 67% |
| Compound B | 17% |
| Compound C | 20% |
| Compound D | 13% |

In the same manner the % of inhibition of the control elastase activity was determined for the compound A at different concentrations The following results were obtained:

| Concentration of compound A | % inhibition of elastase activity tested |
|---|---|
| 0.01% | 53% |
| 0.05% | 50% |
| 0.1% | 68% |
| 0.2% | 68% |

The compound A thus causes a strong inhibition of me elastase activity, even at low concentration.

EXAMPLE 4

The ex vivo activity of the compound of Example 2 was evaluated on surviving human skins treated with human leukocyte elastase (HLE).

The test is performed in the following manner:

Fresh sections of human skins derived from 2 different donors are treated for 2 hours at 20° C. with 20 μl of buffer solution (pH 7.4) containing optionally 10 μg/ml of HLE and optionally 0.1% of the test compound, optionally previously dissolved in ethanol.

The elastin fibres are stained blue with (+) catechol and quantified morphometrically by computer-assisted image analysis. The percentage of mean dermal surface occupied by the elastin fibres is thus evaluated The following results are obtained:

| | % surface occupied by elastin fibres | |
| --- | --- | --- |
| | Skin 1 | Skin 2 |
| Control (untreated skin) | 12.7% | 15.25% |
| Skin treated with HLE | 4.85% | 6.85% |
| Skin treated with HLE + compound of example 2 | 13.95% | 11.85% |

Hence it is observed that the compound according to the invention generates a significant protection of the skins to destruction of the elastin fibres induced by elastase.

EXAMPLE 5

The ex vivo activity of the compound of Example 2 was evaluated on surviving human skins treated with human leukocyte elastase (HLE).

The test was performed in the following manner:

Fragments of normal human skin derived from three different donors are deposited in inserts placed in culture wells. Culture medium supplemented with antibiotics is added to the bottom of the wells. Passage by slow diffusion occurs between the two compartments through the intermediary of a porous membrane (pore size: 12 µm).

The culture medium is renewed every three days.

Optionally 0.5 µg of HLE per ml of culture medium is added to the skin fragments.

5 µl of test compound previously dissolved at 0.2% by weight in ethanol are also added every two days.

The skins are maintained in survival for 10 days at 37° C.

The elastin fibres are stained blue with (+) catechol and quantified morphometrically by computer-assisted image analysis. The mean percentage dermal surface area occupied by the elastin fibres was thus evaluated.

The following results were obtained:

| | % surface occupied by elastin fibres |
| --- | --- |
| Control (untreated skin) | 7.4% |
| Skin treated with HLE | 5.1% |
| Skin treated with HLE + compound of example 2 | 7.1% |

Thus it was observed that the compound according to the invention generates a significant protection of the skins to the destruction of the elastin fibres induced by elastase.

EXAMPLE 6

The activity of the compound of Example 2 was evaluated on irradiated surviving human skins irradiated by UVA (8 J/cm2).

The test is performed in the following manner:

Fragments of normal human skin derived from four different donors are deposited in inserts placed in culture wells. Culture medium supplemented with antibiotics is added to the bottom of the wells. Passage by slow diffusion occurs between the two compartments through the intermediary of a porous membrane (pore size: 12 µm).

The culture medium is renewed every three days.

Every two days 5 µl of the test compound previously dissolved at 0.2% in ethanol are added to the skin fragments.

The skins are maintained in survival for 7 days at 37° C.

The skins are irradiated once only at 8 J/cm2 (Vilbert-Lourmat RMX-3W lamp).

The elastin fibres are stained blue with (+) catechol and quantified morphometrically by computer-assisted image analysis. The mean percentage dermal surface area occupied by the elastin fibres was thus evaluated.

The following results were obtained:

| | Morphometric analysis of elastin fibres (superficial dermis) | Morphometric analysis of collagen (superficial dermis) |
| --- | --- | --- |
| Untreated skin | 6.75% | 87% |
| Skin treated by UVA (8 J/cm$^2$) | 3.9% | 81% |
| Skin treated by UVA (8 J/cm$^2$) + compound of Example 2 | 6.8% | 92% |

It is observed that the compound according to the invention has indeed an activity against the degradation of the elastin fibres in the superficial dermis of the skins irradiated by UVA.

EXAMPLE 7

The activity of different honeys in the in vitro cellular detachment model in man has been compared.

This in vitro screening test of an agent active towards cellular adhesion is carried out on differentiated human keratinocytes. The principle of the test is based on the fact that the inhibition of cellular adhesion induces the release of differentiated human keratinocytes. (The results of this test are comparable to the adhesion of micro-organisms to corneocytes—confirmed in Example 8).

The cellular detachment potency of the test product is greater the larger the number of differentiated keratinocytes released. The test protocol is as follows: starting from biopsies of human skin, after separation of the epidermis from the dermis, the keratinocytes are dissociated by the enzymatic action of trypsin and placed in culture at a concentration of $2 \times 10^5$ cells/ml according to the conventional cell culture techniques known to the specialist skilled in the art. The growth and differentiation of the keratinocytes is obtained by culture for 10 to 20 days.

After removal of the culture medium, the activity of the test product is evaluated. Two samples of culture medium are taken at T0 and T60, i.e. before the addition of the test product (T0) and 60 minutes after this addition (T60). The samples thus taken are analyzed in the flow cytometer in order to count the population of corneocytes present in the medium.

The flow cytometer makes it possible to distinguish the populations of corneocytes and keratinocytes by treatment with acridine orange which is specific for the deoxyribonucleic acid (DNA) of the cells. This stain is specific for the keratinocytes because the corneocytes do not possess nuclei, hence do not have DNA.

The results of these studies are summarised in the following table.

|   | Control | A | B: 0.1% | C: 0.1% | D: 0.1% | E: 0.1% |
|---|---|---|---|---|---|---|
| I | 1958 | 4111 | 2111 | 3055 | 3111 | 4611 |
| II | 0 | 110 | 7.8 | 56 | 58.9 | 135.5 |

Control: Culture medium without compound: negative control
A: 2-hydroxy 5-octanoyl benzoic acid at a concentration of $5 \times 10^{-5}$ M: (Positive control)
B: lavender honey
C: chestnut honey
D: conifer honey
E: acacia honey
I: Number of corneocytes detached (measurement at T60 minus the measurement at T0)
II: Activity of the honeys in % of the control The results confirm the inhibitory activity of the honey on cellular adhesion. The source of the latter seems to be important and acacia honey appears to be the best inhibitor of cellular adhesion.

EXAMPLE 8

The activity of the honey on the adhesion of microorganisms to the skin or to human mucous membranes was measured.

Acacia honey, the most active in the preceding test, was selected for the test in the bacteria/skin adhesion model, as described below.

This ex vivo bacteria/skin adhesion model is based on the use of intact human skin mounted in a sandwich between a bottomless 96 wells plate and a Plexiglas support. The impervious individualized wells make it possible to test in a standard format the effect of acacia honey on the adhesion of *Staphylococcus epidermis* (resident bacteria) to the surface of the skin. The bacteria are radiolabelled in the growth phase by the incorporation of 3H-thymidine. This bacterial flora is then deposited in each well. After incubation for one hour at 20° C., the wells are washed three times with phosphate buffered saline (PBS) in order to remove the free bacteria. The acacia honey is then added at 5 and 10% and incubation allowed to proceed for 1 hour at 20° C. At the end of this incubation the content of each well is recovered and counted in scintillation fluid (desorbed bacteria). The wells are then washed with a chaotropic solution which leads to the elution of the adherent bacteria. The washing solutions are also counted in scintillation fluid (adherent bacteria). The positive and negative controls (Fucogel® acid (poly-[(α-1,3)-Fuc-(α-1,3)-Gal-(α-1,3)-galacturonic]) acid and Bioecolia® (Oligo-[α-1,4)-Gluc-(α-1,2)-Fruc-(α-1,6)-Gluc]) described in the publication of Wolf F. et al. (edition of $19^{th}$ IFSCC Congress, Sydney, 1996) are included in the study as references.

|  | Control | Bioécolia ® (10%) | Fucogel ® (10%) | Acacia honey (5%) | Acacia honey (10%) |
|---|---|---|---|---|---|
| Desorbed bacteria | 100% | 89% (p > 0.05) | 257% (p < 0.01) | 200% (p < 0.01) | 228% (p < 0.01) |
| Adherent bacteria | 100% | 76% (p > 0.05) | 12% (p < 0.01) | 59% (p < 0.01) | 30% (p < 0.01) |

Control: PBS buffer only
p: variance analysis - Dunnett multiple comparison test.

The Fucogel® (positive control) stimulates the desorption of the bacteria and inhibits adhesion. Bioecolia® (negative control) has no significant effect on adhesion. The acacia honey at 5 and 10% stimulates the desorption of the bacteria (228 and 200%) and inhibits adhesion (30 and 59%).

In conclusion, the results presented above confirm the role of acacia honey in the regulation of the adhesion of bacteria to human skin.

This activity is dose-dependent and identical to that off the positive reference.

EXAMPLE 9

The activity of resveratrol on the adhesion of microorganisms to human skin or human mucous membranes was measured.

The activity of resveratrol (3,4',5-trihydroxystilbene) on the adhesion of micro-organisms to human skin or human mucous membranes was tested in a bacteria/skin adhesion model, such as described below.

This ex vivo bacteria/skin adhesion model is based on the use of explants of intact human skin mounted in a sandwich between a bottomless 96 wells plate and a Plexiglas support.

This ex vivo bacteria/skin adhesion model is based on the use of intact human skin mounted in a sandwich between a bottomless 96 wells plate and a Plexiglas support. The impervious individualized wells make it possible to test in a standard format the effect of resveratrol on the adhesion of *Staphylococcus epidermis* (resident bacteria) to the surface of the skin. The bacteria are radiolabelled in the growth phase by the incorporation of 3H-thymidine. This bacterial flora is then deposited in each well. After incubation for one hour at 20° C., the wells are washed three times with phosphate buffered saline (PBS) in order to remove the free bacteria. The acacia honey is then added at 5 and 10% and incubation allowed to proceed for 1 hour at 20° C. At the end of this incubation the content of each well is recovered and counted in scintillation fluid (desorbed bacteria). The wells are then washed with a chaotropic solution which leads to the elution of the adherent bacteria. The washing solutions are also counted in scintillation fluid (adherent bacteria). A positive control (Fucogel® acid (poly-[(α-1,3)-Fuc-(α-1,3)-Gal-(α-1,3)-galacturonic]) acid is included in the study as reference.

|  | Control | Fucogel ® (10%) | resveratrol 0.1 μM | resveratrol 10 μM |
|---|---|---|---|---|
| Adherent bacteria | 100% | 42% (p < 0.01) | 71% (p < 0.01) | 64% (p < 0.01) |

Control: PBS buffer only
p: variance analysis - Dunnett multiple comparison test.

The Fucogel® (positive control) stimulates the desorption of the bacteria and inhibits adhesion. Resveratrol at 0.1 μM and 10 μM inhibits adhesion of the bacteria (29 and 36% of inhibition, respectively).

In conclusion, the results presented above confirm the role of resveratrol in the regulation of the adhesion of bacteria to human skin.

This activity is dose-dependent.

EXAMPLE 10

Composition for Topical Application

The following emulsion is prepared conventionally (% by weight):

| | |
|---|---|
| compound of Example 1 (acid of example 2) | 1% |
| propylene glycol isostearate | 13% |
| polyethylene glycol (8 OE) | 5% |
| propylene glycol | 3% |
| pentylene glycol | 3% |
| glyceryl stearate and polyethylene glycol stearate (100 OE) | 5% |
| oxyethylenated sorbitan monostearate (20 OE) | 0.5% |
| oxyethylenated (20 OE) oxypropylenated (5 OP) cetyl alcohol | 1% |
| gelling agents | 0.5% |
| $C_{12-15}$ alkyl benzoates | 4% |
| ethanol | 3% |
| sodium hydroxide | 0.12% |
| preservatives | qs |
| water | qsp 100% |
| 1-hydroxy-4-methyl 6-(2,4,4-trimethylpentyl)-2 (1H) pyridone-(Octopirox) | 0.25% |
| acacia honey (*Robinia pseudacacia L.*) | 0.5% |

EXAMPLE 11

Face Cream

The following oil-in-water emulsion is prepared conventionally (% by weight):

| | |
|---|---|
| Acacia honey (*Robinia pseudacacia L.*) | 0.5% |
| Compound of Example 2 | 1% |
| Glycerol stearate | 2% |
| Polysorbate 60 (Tween 60 ® sold by the ICI company) | 1% |
| Stearic acid | 1.4% |
| Triethanolamine | 0.7% |
| Carbomer | 0.4% |
| Liquid fraction of karite butter | 12% |
| Perhydrosqualene | 12% |
| Antioxidant | qs |
| Perfume | qs |
| Preservative | qs |
| Water | qsp 100% |

EXAMPLE 12

Dermatological Composition for Topical Application

The following milk is prepared conventionally (% by weight):

| | |
|---|---|
| Vaseline oil | 7% |
| Compound of Example 2 | 1% |
| Glyceryl monostearate, polyethylene glycol stearate (100 OE) | 3% |
| Carboxyvinyl polymer | 0.4% |
| Stearyl alcohol | 0.7% |
| Soya proteins | 3% |
| NaOH | 0.4% |
| Preservative | qs |
| Water | qsp 100% |
| Ketoconazole | 0.5% |
| 5-chloro-2-(2,4-dichlorophenoxyl) phenol-(Triclosan) | 1% |

EXAMPLE 13

Hair Lotion

The following lotion is prepared conventionally (% by weight):

| | |
|---|---|
| 1-hydroxy 4 methyl-6-(2,4,4-trimethylpentyl)-2-(1H) pyridone-(Octopirox) | 0.25% |
| compound of Example 2 | 1% |
| propylene glycol | 23% |
| ethanol | 55% |
| water | qsp 100% |

This lotion can be applied to the scalp of alopecic individuals in order to prevent the effects of UV before and/or after exposure to the sun.

EXAMPLE 14

Anti-hair Loss Lotion

The following lotion is prepared conventionally (% by weight):

| | |
|---|---|
| Compound of Example 2 | 1% |
| propylene glycol | 23% |
| ethanol | 55% |
| Aminexil | 1.5% |
| Water | qsp 100% |
| 1-hydroxy 4 methyl-6-(2,4,4-trimethylpentyl)-2-(1H) pyridone-Octopirox | 0.25% |
| 5-chloro-2-(2,4-dichlorophenoxyl) phenol-(Triclosan) | 0.5% |
| 2,6-diaminopyridine N-oxide (Aminexil) | 2% |

This anti-hair loss lotion can be applied to the scalp of alopecic individuals.

What is claimed is:

1. A cosmetic or dermatological composition comprising:
   (i) an N-acylaminoamide inhibitor of elastase, and
   (ii) at least one compound selected from the group consisting of antifungal agents and antibacterial agents, wherein the inhibitor of elastase is a compound of formula (I):

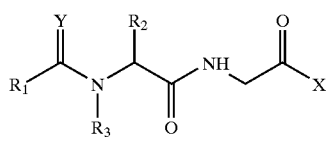

in which:
the Y radical represents O or S,
the R1 radical represents:
(i) a hydrogen atom; or
(ii) a hydrocarbon radical, linear, branched or cyclic, saturated or unsaturated, containing from 1 to 18 carbon atoms,
optionally substituted by 1 to 5 groups, identical or different, selected from
—OH; —OR; —O—COR; —SH; —SR, —S—COR; —NH$_2$; —NHR; —NRR'; —NH—COR; -Hal (halogen); —CN; —COOR; —COR; —P(O)—(OR)$_2$; and —SO$_2$—OR;
with R and R' each representing independently a hydrocarbon radical, linear, branched or cyclic, saturated or unsaturated; containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen); —CN; —COOR"; and —COR";

with R" representing independently a hydrocarbon radical, linear, branched or cyclic, saturated or unsaturated, containing 1 to 6 carbon atoms, optionally halogenated,; or (iii) a radical selected from the radicals —OR; —NH$_2$; —NHR; —NRR'; —NH—COR; —COR; and —COR;

with R and R' each representing independently a hydrocarbon radical, linear, branched or cyclic, saturated or unsaturated, containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR'; —S—COR"; —NH$_2$; —NHR"; —NH—COR"; -Hal (halogen); —CN; —COOK"; and —COR"; with R" representing a hydrocarbon radical, linear, branched or cyclic, saturated or unsaturated, containing 1 to 6 carbon atoms, optionally halogenated, the radical R2 represents a hydrocarbon radical, linear, branched or cyclic saturated or unsaturated, containing 1 to 18 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen); —CN; —COOR; and —COR;

with R and R' each representing independently a hydrocarbon radical, linear, branched or cyclic, saturated or unsaturated, containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —S"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, the radical R3 represents a radical selected from those of formula (II) or (III)

-A-C$_6$H$_{(5-y)}$—B$_y$ (II)

—C$_6$H$_{(5-y)}$—B$_{y'}$ (III)

in which:
y is an integer between 0 and 5, and y' is an integer between 1 and 5;
A is a divalent hydrocarbon radical, linear, branched or cyclic, saturated or unsaturated, containing 1 to 18 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR;

with R and R' each representing independently a hydrocarbon radical, linear, branched or cyclic, saturated or unsaturated, containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, B is a hydrocarbon radical, linear, branched or cyclic, saturated or unsaturated, containing 1 to 18 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR;

with R and R' each representing independently a hydrocarbon radical, linear, branched or cyclic, saturated or unsaturated, containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated,;

the radical X represents a radical selected from —OH; —OR$_4$, —NH$_2$, —NHR$_4$, NR$_4$R$_5$, —SR$_4$, —COOR$_4$; and —COR$_4$;

with R$_4$ and R$_5$ each representing independently a hydrocarbon radical, linear, branched or cyclic, saturated or unsaturated, containing 1 to 6 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen); —CN; —COOR; and —COR;

with R and R' each representing independently a hydrocarbon radical, linear, branched or cyclic, saturated or unsaturated, containing 1 to 6 carbon atoms, optionally halogenated, the R and R' radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH₂; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, the $R_4$ and $R_5$ radicals capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH₂; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, its mineral or organic acid salts, its optical isomers, in isolated form or as a racemic mixture.

2. The composition according to claim 1 in which the compound of formula (I) is such that:

the radical Y represents oxygen, and/or the radical R1 represents hydrogen or a hydrocarbon radical, linear or branched, saturated or unsaturated, containing 1 to 12 carbon atoms, optionally substituted, and/or the substituents of R1 are selected from —OH, —OR and/or —P(O)—(OR)₂ with R representing a hydrocarbon radical, linear, branched or cyclic, saturated or unsaturated, containing 1 to 6 carbon atoms, optionally halogenated; and/or the radical R2 represents a hydrocarbon radical, linear, branched or cyclic, saturated or unsaturated, containing 1 to 12 carbon atoms, optionally substituted; and/or the substituents of R2 are selected from —OH and —OR with R representing a hydrocarbon radical, linear, branched or cyclic, saturated or unsaturated, containing 1 to 6 carbon atoms, optionally halogenated, and/or the radical R3 represents a radical of formula —C₆-H$_{(5-y')}$—B$_y$, for which y'=1, 2 or 3; or a radical of formula -A-C₆H$_{(5-y')}$—B$_y$ for which y=0, 1 or 2; and/or the radical A of R3 is a divalent hydrocarbon radical, linear or branched, saturated or unsaturated, containing 1 to 12 carbon atoms, optionally substituted; and/or the radical B of R3 is a hydrocarbon radical, linear or branched, saturated or unsaturated, containing 1 to 12 carbon atoms, optionally substituted; and/or the substituents of A and/or B are selected from -Hal (halogen); —CN; —COOR; —NO₂; and —SO₂—OR; with R representing a hydrocarbon radical, linear, branched or cyclic, saturated or unsaturated, containing 1 to 6 carbon atoms, optionally halogenated; and/or the radical X represents a radical selected from —OH or OR₄ with R₄ representing a hydrocarbon radical, linear, cyclic or branched, saturated or unsaturated, containing 1 to 6 carbon atoms, optionally substituted;

the substituents of R4 of X are chosen from —OH and —OR with R representing a hydrocarbon radical, linear, branched or cyclic, saturated or unsaturated, containing 1 to 6 carbon atoms, optionally halogenated.

3. The composition according to claim 1, in which the compound of formula (I) is such that:

the radical R1 represents a methyl, ethyl, propyl or isopropyl radical, optionally substituted by an —OH or —P(O)—(OR)₂ group with R representing methyl, ethyl, propyl or isopropyl; and/or the radical R2 represents a methyl, ethyl, propyl, isopropyl, n-butyl, tert-butyl or isobutyl radical; and/or the radical R3 represents a group selected from one of the following formulae:

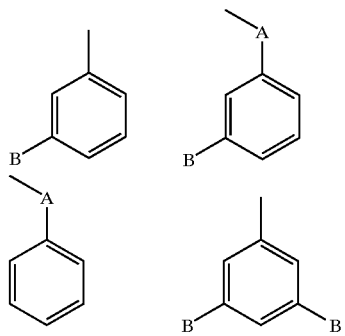

in which the divalent radical A is methylene, ethylene, propylene and/or the radical B is a methyl, ethyl, propyl or isopropyl radical substituted by one or more halogens, and the radical X represents a radical selected from
—OH, —OCH₃, —OC₂H₅, —OC₃H₇ or —OC₄H₉.

4. The composition according to claim 1, comprising at least one of the following:

{2-[acetyl-(3-trifluoromethyl-phenyl)-amino]-3-methyl-butyrylamino} acetic acid;

{2-[acetyl-(3-trifluoromethyl-phenyl)-amino]-3-methyl-butyrylamino} ethyl acetate;

[2-(acetyl-benzyl-amino)-3-methyl-butyrylamino]acetic acid;

[2-(acetyl-benzyl-amino)-3-methyl-butyrylamino]ethyl acetate; and (2-{benzyl-[(diethoxy-phosphoryl)-acetyl]-amino}-3-methyl-butyrylamino)ethyl acetate.

5. The composition according to claim 1, wherein the elastase inhibitor is present in an amount of from 0.00001 to 20% by weight of the total weight of the composition.

6. The composition according to claim 5, wherein the elastase inhibitor is present in an amount of from 0.001 and 10% by weight.

7. The composition according to claim 1, comprising at least one of the following antifungal agents:

imidazole compounds and their derivatives; terbinafine, zinc pirythione, selenium sulfide, tars and the derivatives, undecylenic acid and its salts, 6-cyclohexyl 1-hydroxy 4-methyl 2-(1H)-pyridone or 1-hydroxy 4-methyl 6-(2,4,4-trimethylpentyl)-2-(1H)-pyridone.

8. The composition according to claim 1, comprising at least one of the following antifungal agents:

6-cyclohexyl 1-hydroxy 4-methyl 2-(1H)-pyridone; 1-hydroxy 4-methyl 6-(2,4,4-trimethylpentyl)-2-(1H)-pyridone.

9. The composition according to claim 1, comprising an antifungal agent in an amount of from 0.0001% to 10% of the total weight of the composition.

10. The composition according to claim 9, comprising an antifungal agent in an amount of from 0.01 and 2% of the total weight of the composition.

11. The composition according to claim 1, comprising an antibacterial agent selected from the group consisting of honey, a hydroxystilbene compound, a halogenated antibacterial agent, and a sugar complex.

12. The composition according to claim 1, comprising an antibacterial agent in an amount of from 0.001% to 10% of the total weight of the composition.

13. The composition according to claim 1, comprising an antibacterial agent in an amount of from 0.01% to 2% of the total weight of the composition.

14. The composition according to claim 1, comprising at least one antifungal agent and at least one antibacterial agent.

15. The composition according to claim 14, wherein the weight ratio of the antifungal agent to the antibacterial agent is from 0.2 to 10.

16. The composition according to claim 1 comprising (i) and (ii) in an amount sufficient to care and/or treat ulcerated areas of the skin or areas of the skin subjected to a cutaneous stress or microstress.

17. The composition according to claim 1, in the form of one of the following:
- a product for the care, treatment, cleansing or protection of the skin of the face or body including the scalp and mucous membranes;
- a sun protection composition, an artificial tanning composition (self-tanning) or care composition after exposure to the sun;
- a composition for the hair;
- a care composition for the scalp;
- a product for the make-up of the skin or the face, body or lips; and
- a product for buccal hygiene.

18. The composition according to claim 1 in the form of an anti-wrinkle, anti-age, sun protection, or after-sun composition.

19. A method for treating the skin of the body or face, including the scalp, comprising applying the composition of claim 1 to said skin.

* * * * *

UNITED STATES PATENT AND TRADEMARK OFFICE
CERTIFICATE OF CORRECTION

PATENT NO. : 6,962,712 B2
DATED : November 8, 2005
INVENTOR(S) : Breton et al.

It is certified that error appears in the above-identified patent and that said Letters Patent is hereby corrected as shown below:

<u>Title page,</u>
Insert the following Items:
-- [45] **Date of Patent: \*Nov. 8, 2005**

[\*] Notice: Subject to any disclaimer, the term of this patent is extended or adjusted under 35 U.S.C. 154(b) by 98 days.

This patent is subject to a terminal disclaimer. --.

Signed and Sealed this

Seventh Day of February, 2006

JON W. DUDAS
*Director of the United States Patent and Trademark Office*